United States Patent [19]
Seilhamer et al.

[11] Patent Number: 5,114,923
[45] Date of Patent: May 19, 1992

[54] RECOMBINANT TECHNIQUES FOR PRODUCTION OF NOVEL NATRIURETIC AND VASODILATOR PEPTIDES

[75] Inventors: Jeffrey J. Seilhamer, Milpitas; John A. Lewicki, Los Gatos; Robert M. Scarborough, Belmont; J. Gordon Porter, Newark, all of Calif.

[73] Assignee: California Biotechnology Inc., Mountain View, Calif.

[21] Appl. No.: 460,855

[22] PCT Filed: May 31, 1989

[86] PCT No.: PCT/US89/02373

§ 371 Date: Feb. 2, 1990

§ 102(e) Date: Feb. 2, 1990

Related U.S. Application Data

[63] Continuation-in-part of Ser. No. 299,880, Jan. 19, 1988, abandoned, which is a continuation-in-part of Ser. No. 206,470, Jun. 14, 1988, abandoned, which is a continuation-in-part of Ser. No. 200,383, May 31, 1988, abandoned.

[51] Int. Cl.$^5$ .................. A61K 37/02; C07K 7/08; C07K 7/10
[52] U.S. Cl. .................... 514/12; 530/324; 530/325; 530/326; 530/350; 514/13; 435/69.4
[58] Field of Search .............. 514/12, 13; 530/326, 530/325, 324, 350; 435/69.4

[56] References Cited

U.S. PATENT DOCUMENTS

| 4,496,544 | 1/1985 | Needleman | 514/13 |
| 4,508,712 | 4/1985 | Needleman | 514/13 |
| 4,557,864 | 12/1985 | Needleman | 514/13 |
| 4,607,023 | 8/1986 | Thibault et al. | 514/12 |
| 4,609,725 | 9/1986 | Brady et al. | 530/324 |
| 4,618,600 | 10/1986 | Johnson et al. | 514/12 |
| 4,904,763 | 2/1990 | Matsuo et al. | 530/324 |

OTHER PUBLICATIONS

Kanagawa, et al, Biochem. Biiophys. Res. Commun. 118: 131-139, 1984.
Katsube, et al., Biochem. Biophys. Res. Commun. 128:325-330, 1985.
Maehawa, et al., Biochem. Biophys. Res. Commun., 157: 410-416, 1988.
Minamino, et al., Biochem. Biophys. Res. Commun., 155:740-746, 1988.
Flynn, et al., Biochem. Biophys. Res. Commun., 117:859-865, 1983.
Suggs, et al., Proc. Natl. Acad. Sci., (U.S.A.), 78(11):6613-6617, 1981.
Vlasun, et al., Biochem. Biophys. Res. Commun., 136(1):396-403, 1986.
Oikawa, et al., Biochem. Biophys. Res. Commun., 132(3):892-899, 1985.
Sudoh, et al., Biochem. Biophys. Res. Commun., 155:726-732, 1988.
Sudoh, Nature, 332:78-81, 1988.
Ueda, et al., Biochem. Biophys. Res. Commun., 155:733-739, 1988.
Currie, et al., Science, 223:67-69, 1984.
Kennedy et al., Biochem. Biophys. Res. Commun., 122(3):1076-1082, 1984.
Itoh, et al., Eur. J. of Pharmacology, 150:193-196, Jun. 17, 1988.
Song, et al., FEBS Letters, 232(1):125-129, May 1988.
Dayoff, Atlas of Protein Sequence and Structure, vol. 5:89-99, 1972.
Berent, et al., Bio Techniques, May/Jun. 1985, pp. 208-220.
Hashiguchi, T. et al., FEBS Letters, 236(2):455-461, Aug. 1988.

Primary Examiner—Merrell C. Cashion, Jr.
Assistant Examiner—Susan M. Perkins
Attorney, Agent, or Firm—Morrison & Foerster

[57] ABSTRACT

The cDNA sequence encoding porcine brain natriuretic peptide and related genes encoding canine and human peptides with natriuretic activity are disclosed. The gene is shown to make accessible the DNAs encoding analogous natriuretic peptides in other vertebrate species. The genes encoding these NPs can be used to effect modifications of the sequence to produce alternate forms of the NPs and to provide practical amounts of these proteins. The NPs of the invention can also be (Abstract continued on next page.)

synthesized chemically. The invention peptides have the formula:

$$R^1-Cys-Phe-Gly-Arg-\begin{matrix}Arg/\\Lys\end{matrix}-\begin{matrix}Leu/\\Met\end{matrix}-Asp-Arg- \quad (1)$$

$$Ile-\begin{matrix}Gly/\\Ser\end{matrix}-Ser-\begin{matrix}Leu/\\Ser\end{matrix}-Ser-Gly-Leu-Gly-Cys-R^2$$

wherein $R^1$ is selected from the group consisting of:

(H);

Gly—;

Ser—Gly—;

$$\begin{matrix}Asp\\Lys/\\Gly\end{matrix}-Ser-Gly-;$$

$$\begin{matrix}Arg/\\His/\\Gln\end{matrix}-\begin{matrix}Asp/\\Lys/\\Gly\end{matrix}-Ser-Gly-;$$

$$Met/-\begin{matrix}Arg/\\His/\\Val\end{matrix}-\begin{matrix}Asp/\\Lys/\\Gly\end{matrix}-Ser-Gly-;$$

$$Thr/-Met/-\begin{matrix}Arg/\\His/\\Val\end{matrix}-\begin{matrix}Asp/\\Lys/\\Gly\end{matrix}-Ser-Gly-;$$

$$Lys-\begin{matrix}Thr/\\Met\end{matrix}-\begin{matrix}Met/\\Val\end{matrix}-\begin{matrix}Arg/\\His/\\Gln\end{matrix}-\begin{matrix}Asp/\\Lys/\\Gly\end{matrix}-Ser-Gly-;$$

$$Pro-Lys-\begin{matrix}Thr/\\Met\end{matrix}-\begin{matrix}Met/\\Val\end{matrix}-\begin{matrix}Arg/\\His/\\Gln\end{matrix}-\begin{matrix}Asp/\\Lys/\\Gly\end{matrix}-Ser-Gly-;$$

$$Ser-Pro-Lys-\begin{matrix}Thr/\\Met\end{matrix}-\begin{matrix}Met/\\Val\end{matrix}-\begin{matrix}Arg/\\His/\\Gln\end{matrix}-\begin{matrix}Asp/\\Lys/\\Gly\end{matrix}-Ser-Gly-;$$

or a 10- to 109-amino acid sequence shown as the native upstream sequence for porcine, canine or human NP in FIG. 6, or a composite thereof;

$R^2$ is (OH), $NH_2$, or NR'R'' wherein R' and R'' are independently lower alkyl (1-4C) or is $$\begin{matrix}Asn/\\Lys\end{matrix}$$

$$\begin{matrix}Asn/\\Lys\end{matrix}-Val$$

$$\begin{matrix}Asn/\\Lys\end{matrix}-Val-Leu$$

$$\begin{matrix}Asn/\\Lys\end{matrix}-Val-Leu-Arg$$

$$\begin{matrix}Asn/\\Lys\end{matrix}-Val-Leu-Arg-\begin{matrix}Arg/\\Lys\end{matrix}$$

$$\begin{matrix}Asn/\\Lys\end{matrix}-Val-Leu-Arg-\begin{matrix}Arg/\\Lys\end{matrix}-\begin{matrix}Tyr/\\His\end{matrix}$$

or the amides ($NH_2$ or NR'R'') thereof, with the proviso that if formula (1) is $$R^1\text{-Cys-Phe-Gly-Arg-Arg-Leu-Asp-Arg-}$$
$$\text{Ile-Gly-Ser-Leu-Ser-Gly-Leu-Gly-Cys-}R^2$$

and $R^1$ is Asp-Ser-Gly-, $R^2$ cannot be Asn-Val-Leu-Arg-Arg-Tyr.

The peptides of the invention can be formulated into pharmaceutical compositions and used to treat conditions associated with high extracellular fluid levels, especially congestive heart failure.

4 Claims, 11 Drawing Sheets pBNP cDNA (10-13-88)

```
  1  GAATTCCAGGCTGCTAGGAAGTGAAAAGTGAACCTGACCCAGCTCAGCGGCCAGCAGCGGGCAGCAGG                                              70

71  CAGCAGCCTCTATCCTCTCCAGCCACATGGGCCCCGATGCCGTTCCCGGTGTCCTGCTCCT                                                    140
                            MetGlyProArgMetAlaLeuProArgValLeuLeuLe
                            →

141  GTTCTTGCACCTGTGTGCTAGGATGCCGTTCCATCCACTGGTGCGCTGGCCTGGCTCAGAACTG                                                 210
     uPheLeuHisLeuLeuLeuGlyCysArgHisProLeuGlyGlyLeuAlaSerGluLeu
                                                       -1 +1                                         10

211  CCAGGGATACAGGTGAGCCCTGATGAACTGCTTAGAACTGTTGGTTGGCTGGGAGGGCGGACAGCAAC                                             280
     ProGlyIleGln

281  TAACGGGTCCCCACCTACTGTCCAAGAGGGCTCTAACCTCCTTGGGAACTAGTGATAAGGGGTTAGAA                                             350

351  GGCAGCCAGGCTGGGGTGAGGACCCCGCTCCCAAGGCAGTTGGTCGCTTCAGCACCATCAAGAGTGAT                                             420

421  GGGTCCAGGTGCGAGTTCCTGAGGCTCGGGCTCCCCACCATCCCAGAGCTGCTGACGCCTGCGAG                                                490
                                                              GluLeuLeuAspArgLeuArgA
                                                                                          20.

491  ACAGGGTCTCCGAGCTGCAGGCGGACGGAGCGGACCTGGAGCCCCGGAGGACGTGGCCTCACAGA                                                560
     spArgValSerGluLeuGlnAlaGluArgThrAspLeuArgGluProLeuArgGlnAspArgGlyLeuThrGl
                                          30.                                             40.

561  AGCCTGGAGAGGAGGGAGAGGTTCTTGGGCCCGAGTAGCATCTTCCAAGTCCTC                                                           630
     uAlaTrpGluAlaArgGluAlaAlaProThrGlyValLeuGlyProArgSerIlePheGlnValLeu
                  50.                                                              60.                  70.

631  CGGGAATACGACCCCAAGACGATGCTGACTCTGCTCTTTGGCGGAGGCTGACGCTGGATGGCT                                                   700
     ArgGlyIleArgSerProLysThrMetArgAspSerGlyCysPheGlyArgLeuArgArgLeuAspArgIleGlyLys
                  ↑1                               80.↑2                                         90.

701  CCCTCAGCGGCCTGGGCTGCAATGTGTGAGCACCACCCATTCCCACTGCACGGCCCCGGTTAGCATCAC                                            770
     erLeuSerGlyLeuGlyCysAsnV
              100
```

```
771   TTCTGGGTTTGATGTCTCTGGGACCAAACTCCGAGAAAAGGACACCTGATATCACTCTTCTGTTGC      840
841   CAGTCCTCAAGGCCAAGGAGGCCTTCTGAAAATTAAATTTGGACAGCATTCACTAGCATGACTATG      910
911   AGTCCCCACCCACCTTCTCGCCACCCCTGCCTCTCACCCCAAGGGCAGAATTACTTTAGGATGTAA      980
981   ATTCTGTCATTGCCTGCTGCCTCCTGGGAGCAAAAGAGAACTAAACCTCTCCCCTGGTTTCCCC     1050
1051  TCAACTGTCTGTGGCTGCAAAGGCAGAGGGCAGGATCACCAGGTGATGACAAGTCCCAGCTTACAAGGA  1120
1121  GGAAACTCAGTCCAGAGAGATGGATTATCCCAAAGCCCCAAACATCCAGTTCTGCTGAAGAAGGCGGGT  1190
1191  GGCAGGGGTGGCACGTGGTGGGGGAAGCCCAGTCCTGCCTCTCACCCTAATGTCATCCTCACCC     1260
1261  TCTCTTCTCCCCCACAGTGCTCAGGAGTACTGAGAAGTCCTGGCTGACAACCTCTGTGTCCGTTCTC   1330
                                              alLeuArgArgTyr***
                                                     106
1331  CAACGCCCCTCCCCTGCTCCCCTTCAAAGCAACTCCTGTTTTATTTATGTATTTATTTATTTATTTATT  1400
1401  TGGTGGTTGTATATAAGACGGTTCTATTTGTGAGCACATTTTTCCATGGTGAATAAAGTCAACATTA   1470
1471  GAGCTCTGTCTTTTGAAAAAAAAAAAGGAATTC  1507
```

FIG. 2 : BNP Screening Oligos

```
5'-TCCAGCTGCTTCGGGGGCAGGATGACAGGATTGAGCCCAGAGCCCAGAGCCCAGACTGGCTGTAAC-3'       human ANP
    SerSerCysPheGlyArgMetAspArgIleGlyAlaGlnSerGlyLeuGlyCysAsn-3'                human ANP
    (2)                                                  (21)
           SerGlyCysPheGlyArgArgLeuAspArgIleGlySerLeuSerGlyLeuGlyCysAsn         pig BNP
5'-ACNGGNTGCTTGGGNCGNCTNGACCGNATNGGNTCNCTNTCNGGNCTNGGNTGCAAC-3'                 Pig BNP
    TG         T  A    A  T    TA         AG T  AG         T      T T
                                                                T 3'-AGGCCGACGAAGCCCGGTCCGACCTGTCCTAACCTAGGACTCGCCTGACCCGACATTG-5'    3351  (minimal)

3'-TCGCCCGACGAAGCCCGTCTCTGAGCTGTCTTAGCCGTCGAGTCGCCGAGCCGACGTTG-5'   3352  (G/T pref)

3'-AGGTCGACGAAGCCCCGTCCTACCTGTCCTAACCTCGGGTCTCGCCTGACCCGACATTG-5'   3376  (ANP)
```

Dog NRP Gene 12-12-88

```
  1 CGATCAGGGATGTTGGGCGAGGAAACGGAGGAAGGAGGAGGCCCGAGGACTGTTGTG      70
 71 TCCCCCTCCTGCCCTTTTGGGCCAGGCCCACTTCTATACAAGGCCTGTCTCCAGCCTCCACCCCGGCG     140
141 GGTATGGTGCAGGGCGCGGAGGGCGCCATTCCCCGCCCTGAGCTCAGGGGGAATGCGGCGATAAAT     210
211 CAGAGATAAACCCCAGGGCGGGGATAAGGCGGATAAAAAGCCCGGTGCCGGGATCAGGAGAGCACCCG    280
281 CGCCCCAAGGCGGTGACACTCGACCCGTCCAGCAGCGTGCAGCAGTCAGCAGCCGGAGTCTCTTCCCAC    350
351 TTCTCTCCAGGACATGGAGCCTGCGCAGCCCTGCGCAGCCCGCGGTCCGCCCGGGCCGGAGCCTCGTCTTGCACCT    420
        MetGluProCysAlaAlaLeuProArgAlaLeuLeuLeuPheLeuHisLe
421 GTCGGCCACTCGGAGGCGCCCCACCCGTCGGCGGCGCAGCCCGCTCGGAAGCCTCA     490
    uSerProLeuGlyGlyArgProHisProLeuGlyGlyArgSerProAlaSerGluAlaSer
491 GAAGCCTCGGGGTTGTGCCGGTGCAGGTGAGCCGTGCTCAGCCTGAAGCCGGGGGTGGCAGCAG     560
561 GTCACGGGGGCTTAGCCACTGTCCCAAGTCTCCAGTCTCCCTTGGAATTAGTGATAAGGAATCAGAAA    630
631 GTGACGAGATTGGGTGCCAGGACTCCATACCCAAGGCGGCCAGGCTTCACTGGGTGCAAGGGTGTTCCGC    700
701 CCCGGGCTGGTTCCTGAGGCTGCAGGCCCTCCATTGCAGAGCTGTGGCCGTCTGAAGGACGCAGTTT     770
        GluLeuLeuGlyArgLeuLysAspAlaValS
```

FIG. 3-1

```
771   CAGAGCTGCAGGCAGAGACAGTTGGCCTGGAACCCCTGGAACCGGAGCCACGGAGCCCCAGAAGCCCCGGA    840
      erGluLeuGlnAlaGluGlnLeuAlaLeuGluProLeuHisArgSerHisSerProAlaGluAlaProGl
841   GGCCGGAGGAACGCCCCGTGGGGTCCTTGCACCCCATGACACAGTGTCCTCCAGCCCTGAGAAGACTACGC    910
      uAlaGlyGlyThrProArgGlyValLeuAlaProHisAspSerValLeuGlnAlaLeuArgArgLeuArg
911   AGCCCCAAGATGATGCACAAGTCAGGTGCTTTGGCCGGACGCTGACCGGATCGGCTCCTCAGTGGCC      980
      SerProLysMetMetHisLysSerGlyCysPheGlyArgArgLeuAspArgIleGlySerLeuSerGlyL
981   TGGGCTGCAATGGTAAGCCGCTCCTGCGCGCCTTGGCTCCCCAGCCCCTGGCTTCGACCCTT           1050
      euGlyCysAsnV
1051  GGAACCCCTTCTGGGTTTGTTGTCTCGGGGATCACACTCTGAGGAAAGGACATCTGGACATGCTCCTT    1120
1121  CTTGCTGACAGTCCTAAGGGCCAAGGAGTACGTTCTGGAAATACTACGTGTGGACATGTGTCCAGGG    1190
1191  TCCCTACCCACCTCCTAGCCCCTCCTCGCCTCTCGCACCCAAAGGGCAGAATCATCTTAGGATGAATCA    1260
1261  GTCGTTGTCTGGAAGCATCTCCTTGGAGCAGAAAGAGTCCTAAACATGTCCTGTAGCTCTCTCTGTCT    1330
1331  GTCTGTAGCCACGAAGGCAGAGGTCAGGTGCACCAGGGCAGTGATGATTCCCAGTTAACAGAGGAGGAGA  1400
1401  CTGAGGTCTAGAGAGATGATTATTCCAAAGCCTCAAACATCCAGATCGGCTGAGGGTGGGGTTGGTGGC   1470
1471  AGGGATGGCTCTGGGAAGCTCGGATCCTCAGTCTCCCACCTGACGCCATCATCCCCTC              1540
1541  TCTCCTCCCACAGTGCTGAGAAAGTATTAAGGAGGAAGTCCGACTGCCACATTCTGCATTGATTCT      1610
```

FIG. 3-2

```
                alLeuArgLysTyr***
1611  TCAGCAGCCCCTGAGCCCCTTGGAAGCAGATCTTATTTATTCGTATTTATTTATTTATTTCGATTG  1680
1681  TTTTATATAAGATGATCCTGACGCCCGAGCACGGATTTCCACGGTGAAATAAGTCAACCTTAGAGCTT  1750
1751  CTTTGAAACCGATTGTCCCTGTGCATTAAAAGTAACACATCATTAAAAAAA  1804
```

Human NRP Gene 12-12-88

```
    1  CCCACGGTGTCCCGAGGAGGAGCACCCCGCAGGCTGAGGGCAGGTGGGAAGCAAACCCGGACG                                              70
   71  CATCGCAGCAGCAGCAGCAGCAGCAGCCTCCGCAGTCCCTCCAGAGACATGGATC                                                    140
                                                                    MetAspP
  141  CCCAGACAGCACCTTCCCGGGGCTCCTGCTCTCTTGCATCTGGCTTCCTGGAGGTCGTC                                                210
       roGlnThrAlaProSerArgAlaLeuLeuLeuLeuPheLeuHisLeuAlaPheLeuGlyArgSe
  211  CCACCCGCTGGGCAGCCCCGGTTCAGCCTGGACTTGGAAACGTCCGGGTTACAGTGAGAGCGGAGGGC                                      280
       rHisProLeuGlySerProGlySerAlaSerAspLeuSerGluThrSerGlyLeuGln
  281  AGCTCAGGGGATTGACACAGCAATGAAAGGTCCTCACCTGCTCCCAAGAGCCCTCATCTTTCC                                            350
  351  TTTGGAATTAGTGATAAAGGAATCAGAAAATGAGAGACTGGTGCCCTGACCCTGTACCAAGGCAGTC                                       420
  421  GGTTCACTTGGGGTGCCATGAAGGGCTGTTGAGCCAGGGTGGGTCCCTGAGGCTTGGACGCCCCATTCA                                     490
  491  TTGCAGGAGCAGCCAACCATTTGCAGGGCAAACTGTCCAGGCGTGCAGGTGGAGCAGCAGACATCCCTGGAGC                                 560
       GluGlnArgAsnHisLeuGlnGlyLysLeuSerGluLeuGlnValGluLeuGlnThrSerLeuGluP
  561  CCCTCCAGGAGAGCCCCCTCCCACAGTTGCTGGAAGTCCCGGAGTAGCCACCGAGGGCATCCGTGG                                        630
       roLeuGlnGluSerProArgProThrGlyValTrpLysSerArgGluValAlaThrGluGlyIleArgGl
  631  GCACCGCAAAATGTCCTCTACACCCTGCGGGCCACGAAGCCCAAGATGTGCAAGGGTCTGGCTGC                                          700
       yHisArgLysMetValLeuTyrThrLeuArgAlaProArgSerProLysMetValGlnGlySerGlyCys
```

FIG. 5-2

```
701  TTTGGAGGAAGATGACCGATCAGTCCTCCAGTGGCTGGCTGCAAAGGTAAGCACCCCTGCCAC   770
     PheGlyArgLysMetAspArgIleSerSerSerGlyLeuGlyCysLysV
771  CCCGGCCGGCCTTCCCCCATTCCAGTGTGTGACACTGTAGAGTCACTTGGGGTTTGTGTCTGGGAA   840
841  CCACACTCTTTGAGAAAAGGTCACCTGACATGCTTCCTCTGTTAACAGCCTTCAGGGCCAAGGGGTG   910
911  CCTTTGTGGAATTAGTAAATGGGCTTATTCATTACCATGCCCACATACCTTCTCCCACCTCCTAC   980
981  TTCTTATCAAAGGGGCAGAATCTCCTTGGGGTCTGTTATCATTTGGCAGCCCCCAGTGGTGCAGAA  1050
1051 AGAGAACCAAACATTCCTCCGTTCCTCTAAACTGTCTATAGTCTCAAAGGCAGAGAGCAGGATCAC  1120
1121 CAGAGCAATGATAATCCCAATTTACAGATGAGGAAACTGAGGCTCAGAGAGTTGCATTAAGCCTCAAAC  1190
1191 GTCTGATGACTAACAGGGTGGTGGCCACACGATGAGGTAAGCTCAGCCCCTGCCTCCATTCCCACC  1260
1261 CTAACCATCATCACCCCTCTCTTCCCTGACAGTGCTGAGGGGCTGAGGGGCATTAAGAGGAAGTCCTGGCTGCAG  1330
     aLeuArgArgHis***
1331 ACACCCTGCTTCTGATTCCACAAGGGCTTTTCCTCAACCCTGTGGCCCTGCCCTCATCTTTCCTTTGGAATTAG  1400
1401 TGATAAAGGAATCAGAAATGCAGACGAGACTGGTGCCCTGACCCTCTACCCAAGGCAGTCGGTTCACTTGG  1470
1471 GTGCCCATGAAGGGCCTGGTGAGCCAGGGGTTGGGTCCCTGAGGCTTTTA  1519
```

FIG. 6-1

|   | | | | | | | | | | 10 | | | | | | | | | | 20 |
|---|---|---|---|---|---|---|---|---|---|---|---|---|---|---|---|---|---|---|---|---|
| 1 Pig PreproBNP | Met | Gly | Pro | Arg | Met | Ala | Leu | Pro | Arg | Val | Leu | Leu | Leu | Phe | Leu | His | Leu | Leu | Leu | Leu |
| 2 Dog PreproNRP | --- | Glu | --- | --- | Cys | Ala | --- | --- | --- | Ala | --- | --- | Leu | --- | --- | --- | --- | --- | Ser | Pro |
| 3 Human PreproNRP | --- | Asp | --- | --- | Gln | Thr | --- | Pro | Ser | Ala | --- | --- | --- | --- | --- | --- | --- | --- | Ala | Phe |

|   | | | | | | | | | | 30 | | | | | | | | | | 40 |
|---|---|---|---|---|---|---|---|---|---|---|---|---|---|---|---|---|---|---|---|---|
| 1 | Leu | Gly | Cys | Arg | Ser | His | Pro | Leu | Gly | Ala | Gly | Leu | Ala | Ser | Glu | Leu | Pro | Gly | Ile |
| 2 | --- | --- | Gly | --- | Pro | --- | --- | --- | --- | --- | Arg | Ser | Pro | --- | --- | --- | Ala | Ser | Glu | Ala |
| 3 | --- | --- | Gly | --- | --- | --- | --- | --- | --- | --- | Ser | Pro | --- | --- | Asp | --- | Glu | Thr | Ser |

↓SP

|   | | | | | | | | | | 50 | | | | | | | | | | 60 |
|---|---|---|---|---|---|---|---|---|---|---|---|---|---|---|---|---|---|---|---|---|
| 1 | Gln | Glu | Leu | Leu | Asp | Arg | Leu | Arg | Asp | Arg | Val | Ser | Glu | Leu | Gln | Ala | Glu | Arg | Thr | Asp |
| 2 | Ser | --- | --- | --- | Gly | --- | --- | Lys | --- | Ala | --- | --- | --- | --- | --- | --- | Gln | Leu | Ala |
| 3 | Gly | --- | --- | Gln | Arg | Asn | His | --- | Gln | Gly | Lys | Leu | --- | --- | --- | Val | --- | Gln | --- | Ser |

↓1 ↑Leu Gln

FIG. 6-2

```
                                              70                              80
Leu Glu Pro Leu Arg Gln Asp Arg Gly Leu Thr Glu Ala Trp Glu Ala Arg Glu Ala Ala
---     ---     ---     His Arg Ser His Ser Pro Ala ---  Pro ---  Gly Gly Thr
---     ---     Gln Glu Ser Pro Arg Pro ---  Gly Val ---  Lys Ser ---  Val 90                             100
Pro Thr Gly Val Leu Gly Pro Arg Ser Ser Ile Phe Gln Val Leu Arg Gly Ile Arg Ser
---  Arg ---     ---     Ala ---  His Asp ---  Val Leu ---  Ala ---     Arg Leu ---
---  Thr Glu ---     ---  Ile Arg Gly His ---  Lys Met Val Leu Tyr Thr ---  Ala Pro
                                                                              ↑1
                                             110                             120
Pro Lys Thr Met Arg Asp Ser Gly Cys Phe Gly Arg Arg Leu Asp Arg Ile Gly Ser Leu
---  Met ---     ---  His Lys ---     ---     ---     ---     Lys Met ---     ---
---     Met Val Gln Gly ---     ---     ---     ---     ---     ---     Ser Ser
        ↑?

130 131
Ser Gly Leu Gly Cys Asn Val Leu Arg Arg Tyr
---     ---     ---     ---     ---  Lys ---
---     ---     ---     ---  Lys ---  His
```

RECOMBINANT TECHNIQUES FOR PRODUCTION OF NOVEL NATRIURETIC AND VASODILATOR PEPTIDES

CROSS-REFERENCE TO RELATED APPLICATION

This is a continuation-in-part of U.S. Ser. No. 299,880, filed 19 Jan. 1989, now abandoned, which is a continuation-in-part of U.S. Ser. No. 206,470, filed 14 Jun. 1988, now abandoned, which is a continuation-in-part of U.S. Ser. No. 200,383, filed 31 May 1988, now abandoned.

TECHNICAL FIELD

The invention relates generally to natriuretic and/or vasodilator peptides found in brain and cardiac tissue. More particularly, it relates to the gene encoding a natriuretic and/or vasodilator peptide obtained from porcine tissue and genes encoding peptides related by amino acid sequence in other species. Most particularly, it relates to the gene encoding natriuretic and/or vasodilator peptide from human atria.

BACKGROUND ART

The existence of peptides in the atrium which are responsible for maintenance of normal extracellular fluid parameters—i.e., the volume and pressure of liquid in the blood vessels—is well known. A series of closely related peptides, designated atrial natriuretic peptides, have been isolated from several species and identified, and analogs of these peptides have been prepared.

The natriuretic effect of a crude extract of rat atrial tissue was demonstrated over seven years ago. A number of peptides with diuretic and natriuretic properties have since been isolated from atrial tissue and sequenced: Flynn, T.G., et al., *Biochem Biophys Res Commun* (1983) 117:859-865; Currie, M.G., et al., *Science* (1984) 223:67-69; Kangawa, K., et al., *Biochem Biophys Res Commun* (1984) 118:131-139; U.S. Pat. No. 4,496,544; U.S. Pat. No. 4,508,712; Kangawa, K., et al., *Biochem Biophys Res Commun* (1984) 119:933-940; Garcia, R., et al., *Biochem Biophys Res Commun* (1985) 126:178-174; Katsube, N., et al., *Biochem Biophys Res Commun* (1985) 128:325-330; U.S. Pat. Nos. 4,607,023; 4,557,864; and 4,618,600; copending applications 616,488, now abandoned; 766,030, now U.S. Pat. Nos. 4,764,504; and 870,795. These peptides, called atrial natriuretic peptides (ANPs), are cyclic disulfides comprising 17 amino acids in the cycle (including the two cysteines which provide the disulfide bond). The gene which encodes them encodes a larger protein which is then processed into shorter versions which make up the set of ANPs.

Various analogs of the isolated atrial peptides are also described in copending application Ser. Nos.921,360, now abandoned; 138,893; now abandoned; and 174,739now U.S. Pat. No. 4,935,492.

It is understood that these peptides and their analogs are effective in regulating blood pressure by controlling fluid volume and vessel diameter. A number of disease states are characterized by abnormal fluid retention, including congestive heart failure, cirrhosis of the liver, and nephrotic syndrome. These diseases are associated with excessive fluid accumulation on the venous side of circulation, and an underperfusion of the kidneys, leading to a fall in glomerular filtration rate (GFR). In addition, reduced renal perfusion stimulates secretion of renin, a proteolytic enzyme which, in the circulation, leads to the formation of angiotensin, a powerful constrictor of the arteriole. Renin also stimulates release of the sodium-retaining hormone aldosterone by the adrenal gland.

Hypertension per se is another serious result of an increase in extracellular fluid volume and is a major cause of death.

Therapeutic measures related to diseases associated with sodium and water retention are varied and include administration of a variety of diuretic substances. However, no single therapeutic agent is satisfactory for all individuals, and it is important to enhance the repertoire of available materials. The present invention provides additional materials which, besides their supplementation of the repertoire of useful therapeutics, are important in that they are found in brain and atrium and thus may shed light on the central and peripheral mechanisms whereby normal individuals maintain the appropriate fluid balance. In addition, some of these peptides and proteins have modified and altered physiological activities.

One of these factors from porcine brain has been isolated and sequenced by Sudoh, P., *Nature* (1988) 332:78-81. It is a 26-amino acid peptide synthesized in porcine brain and atrial tissue. In atrial tissue, the peptide is present at about 1/100 of the concentration of analyzed atrial natriuretic peptide (ANP) activity. However, in brain the peptide may be more abundant than ANP. The spectrum of activity of this porcine brain natriuretic peptide, or pBNP, is similar to that of the porcine ANP. A comparison of the amino acid sequences of a portion of human ANP (hANP) and the pBNP is shown below; the corresponding relevant portion of the porcine ANP is identical to the human sequence

```
       102
hANP   Arg—Ser—Ser —Cys—Phe—Gly—Gly—Arg—Met—Asp—Arg—Ile—
pBNP   Asp—Ser—Gly—Cys—Phe—Gly—Arg—Arg—Leu—Asp—Arg—Ile—
       *1              *          *    *

126
Gly—Ala—Gln—Ser—Gly—Leu—Gly—Cys—Asn—Ser—Phe ------- Arg—Tyr
Gly—Ser—Leu—Ser—Gly—Leu—Gly—Cys—Asn—Val—Leu—Arg—Arg—Tyr
  *    *                           *    *               26
```

There are nine (starred) positions which are not homologous. The conservative substitution of Leu for Ile or Met, found in rat or human ANP sequences, respectively, is a known acceptable substitution.

Subsequent papers from this same group at Miyazaki Medical College further characterize these proteins. Sudoh, T., et al., *Biochem Biophys Res Comm* (1988) 155:726-732, report the isolation of a 32-amino acid natriuretic peptide ("BNP-32") from porcine brain which contains the 26 amino acids of the porcine BNP described above at its C-terminus and an additional N-terminal 6-amino acid extended portion of the sequence Ser-Pro-Lys-Thr-Met-Arg-. In papers following on subsequent pages, levels of various natriuretic peptides in tissues are reported. Ueda, S., et al., (ibid.), pp. 733-739, utilized a radioimmunoassay to localize and measure the levels of porcine BNP and porcine BNP-32 in the brain and spinal cord. The results showed that both BNP and BNP-32 were major forms of immunoreactive BNP in the porcine brain, and that the highest concentrations were found in the medulla-pons, striatum, and spinal cord. The porcine form of atrial natriuretic peptide (pANP) was also found in the porcine brain but at a level approximately 13 times lower than that characteristic of BNP. Minamino, N., et al. (ibid.), pp. 740-746, report the results of radioimmunoassay for porcine BNP and ANP in peripheral tissue. The concentration of BNP was highest in cardiac atrium of the tissues assayed. The immunoreactive form of this protein was characterized as mostly a 12 kd high molecular weight form; less than 15% of the total immunoreactive BNP in atrial tissue is of the lower molecular weight forms pBNP or pBNP-32.

In a subsequent issue of this publication, Minamino, N., et al., *Biochem Biophys Res Comm* (1988) 157:402-409, reported the isolation and characterization of this higher molecular weight form of BNP from porcine heart. The complete amino acid sequence of this protein was obtained and shown to contain the 26-amino acid pBNP (and 32-amino acid pBNP-32) at its carboxy terminus. The full-length protein contains 106 amino acids. Finally, Maekawa, K., et al. (ibid.), pp. 410-416, report the cloning and sequence analysis of a cDNA. encoding a precursor protein for porcine BNP. A cDNA library was obtained from porcine cardiac atrium and the relevant BNP-encoding gene was isolated and sequenced. The gene was found to include a 25-residue putative signal peptide at the N-terminus followed by the codons corresponding to the 106 amino acids of the reported protein.

These results are consistent with the information available from studies of the atrial-derived natriuretic peptides which are generally also associated with longer precursors. In the parent application herein, the gene encoding porcine BNP was provided, which permitted the putative amino acid sequence of the upstream portion of these precursor proteins to be deduced. While the cDNA obtained in the parent application was incompletely processed and contained an intron, further manipulation of this sequence using standard techniques as described below permitted the location of the intron to be established. The parent application disclosed a straightforward procedure which could be applied to identify natriuretic-related peptides (NRP) from other species. The direct procedure outlined did not permit cloning of human NRP. As will be discussed further below, it was not possible to obtain human NRP using only porcine BNP as a probe. It was necessary to use an intermediary clone, canine BNP, to obtain human NRP. Accordingly, the invention provides a family of natriuretic peptides (NPs) and natriuretic-related peptides (NRPs) from a variety of vertebrate source.

DISCLOSURE OF THE INVENTION

The invention provides the complete gene sequence for pBNP and the prepro form thereof and thus the ability to synthesize large amounts of the proteins encoded by this gene and modified forms thereof. The invention also enables retrieval of the gene sequences encoding similar proteins having natriuretic activity from other vertebrate species, and thus provides the ability to synthesize them as well. The cDNA encoding the porcine BNP and its precursors and perhaps shorter associated brain proteins is shown in FIG. 1; the segment of this "unprocessed" cDNA which encodes the 26 amino acid pBNP described by Sudoh (supra) is underlined.

Accordingly, in one aspect, the invention is directed to a recombinant cDNA probe containing the sequence encoding the 26-amino acid natriuretic peptide of porcine brain, which comprises the DNA of FIG. 1 or an effective portion thereof. The invention is also directed to recombinant DNA sequences retrieved using this probe, or probes derived from it, and thus includes alternatively useful probes which comprise effective portions of the coding sequences for peptides from canine and human sources shown in FIG. 3 and 5.

In another aspect, the invention is directed to peptides having natriuretic activity of the formula:

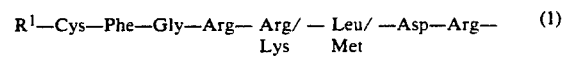
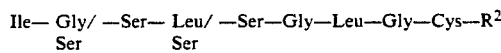

wherein $R^1$ is selected from the group consisting of:

(H);

Gly—;

Ser—Gly—;

Asp
Lys/ —Ser—Gly—;
Gly

Arg/    Asp/
His/ — Lys/ —Ser—Gly—;
Gln     Gly

Arg/    Asp/
Met/ — His/ — Lys/ —Ser—Gly—;
Val      Gln     Gly

Arg/    Asp/
Thr/ — Met/ — His/ — Lys/ —Ser—Gly—;
Met    Val    Gln     Gly

Arg/    Asp/
Lys— Thr/ — Met/ — His/ — Lys/ —Ser—Gly—;
      Met    Val    Gln     Gly

Arg/    Asp/
Pro—Lys— Thr/ — Met/ — His/ — Lys/ —Ser—Gly—;
          Met    Val    Gln     Gly

Arg/    Asp/
Ser—Pro—Lys— Thr/ — Met/ — His/ — Lys/ —Ser—Gly—;
              Met    Val    Gln     Gly or a 10- to 109-amino acid sequence shown as the native upstream sequence for porcine, canine or human BNP in FIG. 8, or a composite thereof;

$R^2$ is (OH), $NH_2$, or $NR'R''$ wherein $R'$ and $R''$ are independently lower alkyl (1-4C) or are Asn/
Lys -continued Asn/ —Val
Lys Asn/ —Val—Leu
Lys Asn/ —Val—Leu—Arg
Lys Asn/ —Val—Leu—Arg— Arg/
Lys                   Lys Asn/ —Val—Leu—Arg— Arg/ — Tyr/
Lys                   Lys    His or the amides ($NH_2$ or NR'R'') thereof, with the proviso that if formula (1) is $R^1$-Cys-Phe-Gly-Arg-Arg-Leu-Asp-Arg-Ile-Gly-Ser-Leu-Ser-Gly-Leu-Gly-Cys-$R^2$ and $R^1$ is Asp-Ser-Gly-, $R^2$ cannot be Asn-Val-Leu-Arg-Arg-Tyr.

In other aspects, the invention is related to recombinant DNA sequences encoding the foregoing peptides and to recombinant expression systems capable of production of these peptides in suitably transformed hosts. The invention is also related to methods to produce the peptides of the invention using recombinant means by culturing the transformed cells and recovering the desired peptide from the cell cultures.

The invention is also directed to modified forms of this class of peptides wherein 1 or 2 of the positions contain conservative amino acid substitutions.

The invention also relates to pharmaceutical compositions and methods of treatment using the peptides of the invention.

BRIEF DESCRIPTION OF THE DRAWINGS

FIG. 1-1 to 1-2 shows the complete sequence of a retrieved cDNA in unprocessed form which encodes porcine BNP with the location of the intron established. The portion of the sequence which encodes the 26-amino acid pBNP peptide is underlined and consists of nucleotide residues 660-723 and 1276-1289 inclusive.

FIG. 2 shows oligonucleotides synthesized as probes for pBNP-encoding cDNA.

FIG. 3-1 to 3-3 shows the DNA and deduced protein sequence for the coding portions of the gene encoding a canine protein with natriuretic activity.

FIG. 5-1 to -5-2 shows the DNA and deduced amino acid sequence of the human genomic clone encoding the human NRP.

FIG. 6-1 to 6-2 shows a comparison of the amino acid sequences of the prepro forms of the porcine, canine and human proteins of the invention.

MODES OF CARRYING OUT THE INVENTION

A. Definitions

Figure 4:
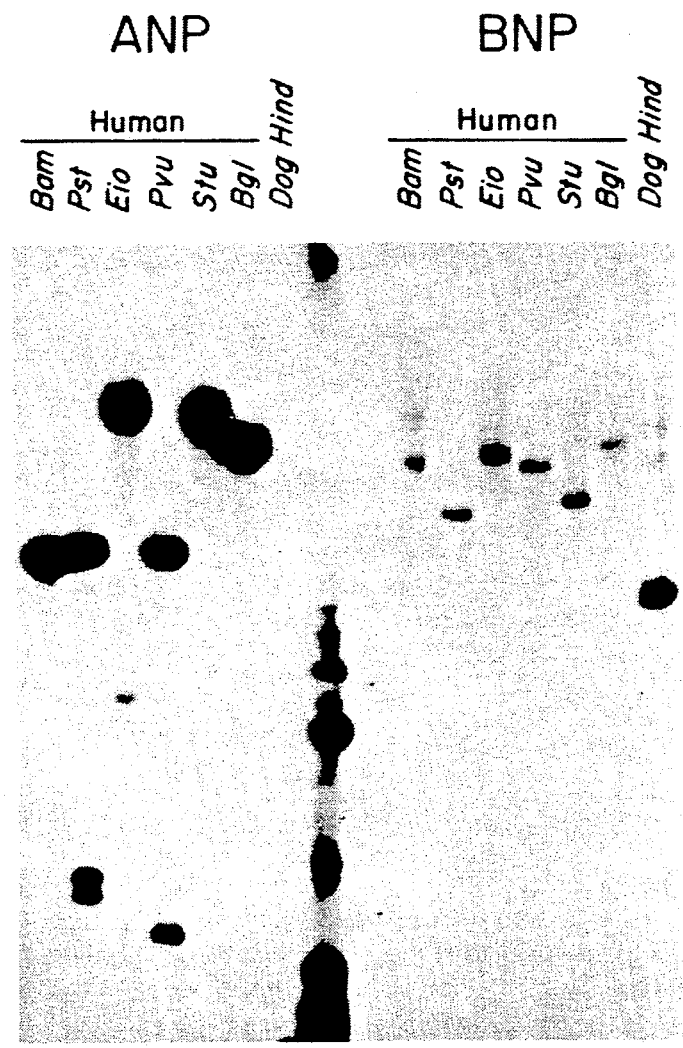
FIG. 4 shows Southern blots of human genomic DNA probed with human ANP (left panel) and with canine NRP (right panel).

As used herein, "brain natriuretic peptide (BNP)" refers to an amino acid sequence which is encoded by a DNA capable of hybridizing to an effective portion of the DNA shown in FIG. 1 under defined stringency conditions, and which has natriuretic activity. It is believed that the brains of all vertebrates contain a subpopulation of peptides with this activity which comprise peptides analogous to that disclosed herein as pBNP and longer precursor proteins containing this amino acid sequence, as well as active fragments thereof.

As used herein, "porcine brain natriuretic peptide (pBNP)" refers to the 26 amino acid sequence isolated by Sudoh et al., and set forth hereinabove. "pBNP-encoding cDNA" refers to the nucleotide sequence shown in FIG. 1 herein, comprising residues 660-723 and 1276-1289 inclusive. The separation in the cDNA of the pBNP codons is presumably due to incomplete processing of the mRNA which formed the template for this particular clone. This clone was deposited at the American Type Culture Collection, Rockville, Md., on 10 Jun. 1988 and has accession number ATCC 40465.

The pBNP-encoding cDNA shown in FIG. 1, because it contains additional sequences encoding precursor proteins, and, as explained below, presumably contains nucleotides corresponding to an additional intron besides that represented by the sequence separating the pBNP-encoding portion per se, may be used as an effective probe to obtain either genomic or cDNA sequences encoding corresponding associated brain natriuretic peptides in some other vertebrate species. "Precursor brain natriuretic peptide" as used in the present application refers to peptides with natriuretic activity encoded by the gene sequence from which, for example, the pBNP protein is derived but processed so as to obtain peptides of different length. Similar processing differences presumably exist in other vertebrates as well; the entire class of such natriuretic peptides is retrieved by the DNA probe of the invention. For example, examination of the reading frame of the pNP-encoding DNA shows an N-terminal extension so that N-terminally extended peptides can be postulated. It has been shown that the ANP precursor "pro-ANP" is processed differently in atrial and brain tissues leading to different ANP peptides. By analogy to the peptides found in the atrium, it is postulated that an important peripheral form of BNP would be the 29-residue peptide of pBNP N-terminally extended with the tripeptide Thr-Met-Arg. Further N-terminal extended peptides with the additional upstream residues Ser-Pro-Lys and Gly-Ile-Arg-Ser-Pro-Lys are also expected. Thus, examination of the reading frame which contains the pBNP also permits postulation of additional upstream processing sites which would extend the N-terminal sequence further.

Other extended precursor peptides are discoverable through standard techniques using the sequence information of FIG. 1. It is clear, by analogy with atrial natriuretic peptide precursors, that the start of the longest precursor, perhaps including a signal sequence, is at the methionine codon shown in the uppermost reading frame in the line spanning nucleotide 61 and 120, or at the closely positioned downstream ATG. Therefore, it is clear that the reading frame is not maintained from this start of translation into the pBNP-encoding region. This indicates that there is at least one other intron transcribed into the cDNA clone retrieved. The location of this intron and deduction of the full sequence for the longest form of precursor peptide is described in further detail below. In any event, precursor BNP peptides associated with pBNP include other natriuretic peptides encoded by this depicted gene; analogous groups of peptides are collectively designated natriuretic peptides (NPs) and include "natriuretic-related peptides" (NRPs) in other species.

Additional terminology which is useful is the term "prepro" NRP, which refers to the encoded peptide having both the native associated signal sequence which effects secretion of the various forms of the peptide with natriuretic activity and an amino acid sequence of the secreted peptide which is fused upstream of the cyclic portion absolutely required for this activity The "pro" form having the upstream sequence may represent the circulating form of the peptide. With respect to the three specific embodiments included within the present invention, which are shown in detail in FIGS. 1, 3, and 5 for porcine, canine and human proteins, respectively, the location of the putative signal sequences representing the "pre" sequence is shown in each figure, as well as the full-length mature protein, which is thought to be a precursor form designated the "pro" form. Because various processing sites are available, as indicated by the upward-pointing arrows in these figures and in the composite sequences shown in FIG. 6, attempts to make a fine-line and definite distinction between the "pro" NP and "NP" are probably meaningless. The peptides defined by the invention are set forth in formula (1) above and have natriuretic and/or vasodilator activity, regardless of the length of the N-terminal form preceding the identified 26-amino acid regions corresponding to the porcine "BNP" of Sudoh, or attached to the cyclic portion thereof.

"Expression system" refers to a DNA which contains a coding region operably linked to suitable control sequences capable of effecting its expression in a compatible host. Expression systems invariably comprise a promoter, but, depending on the host intended, may contain additional critical DNA such as ribosome binding site or CAP site, termination sequence, and optional enhancer sequences upstream from the promoter or in other operable locations. The recombinant expression systems of the invention herein comprise a DNA of the invention encoding a BNP, for example, a BNP derived from a vertebrate source, operably linked to additional DNA sequences which are capable of effecting its expression. The expression system may reside on a transfer vector such as a plasmid or a viral vector which is self-replicating independently of the chromosome of the host cell, or may be constructed so that when inserted into a host cell it is able to integrate into the chromosome.

B. Other Associated Porcine BNPs and Retrieval of Vertebrate NRP Genes

The invention, in one aspect, is directed to all members of the group of porcine BNP proteins encoded in the cDNA shown in FIG. 1, and to conservative modifications thereof. The deduction of the amino acid sequence encoding the longest precursor protein, and therefore deduction of the processed forms, can be accomplished using the unprocessed cDNA here provided. In this standard approach, oligonucleotide sequences representing short portions of the cDNA spanning the potential intron—i.e., between residues 100 to about 660—are synthesized, labeled, and used to probe Northern blots of mRNA isolated from cells producing BNP. Most mRNAs will be in processed form; hence, those oligonucleotides which successfully hybridize to the proper length message represent coding regions of the cDNA. Those which do not readily hybridize represent intron regions. By using overlapping synthetic cDNAs, the intron position can be precisely identified. This permits deduction of the complete sequence encoding the largest precursor protein, and defines the sequence from which the associated BNP proteins are formed.

In a modification of this approach, partial cDNA fragments were generated in amplified form from mRNA isolated from porcine atrium. The cDNA for amplification was obtained by hybridization of poly A+ RNA isolated from this tissue with the oligonucleotide 3895. Amplification was performed using a polymerase chain reaction wherein the oligonucleotide primers corresponded to bases 100-123 (identity strand) and 652-685 (complementary strand) as shown in FIG. 1. Two bands are obtained when the amplified products are analyzed on preparative agarose gels; the larger band in low relative abundance presumably represents the smaller DNA derived from the unspliced precursor, and the more prominent band is assumed to be the more fully processed cDNA. When this band was eluted from the gel and sequenced, the stretch corresponding to bases 223-468 of FIG. 1 was not present, and the recovered DNA had the sequence shown in FIG. 3.

Thus, using standard techniques, the location of the putative upstream intron, which would correspond to that found in atrial natriuretic peptide precursors, as described by Greenberg et al., *Nature* (1984) 312:656-658, was easily obtained. As indicated in FIG. 1, a reading frame of 131 amino acids is obtained. It is believed that the signal sequence is represented by amino acids 1-25, and that the cleavage site converting the prepro form of porcine BNP to the pro form is between $Ser_{25}$ and His at position 26 of the prepro sequence. The sequence of the porcine BNP reported by Sudoh having 26 amino acids is represented by amino acid residues 81-106 (106-131).

In addition to providing access to the class of porcine BNPs encoded on the retrieved cDNA, the cDNA of FIG. 1 provides access to the corresponding precursor gene encoding the class of associated NRP proteins from various vertebrate species.

The pBNP-encoding cDNA shown in FIG. 1, or an effective portion thereof can be used as a probe in gene libraries obtained from other vertebrate hosts, by a number of procedures generally known in the art. There was every reason to believe that porcine BNP should be capable of hybridizing to human NRP under appropriate conditions; however no conditions could be determined under which pBNP would hybridize to a human library. This was surprising in that, in an evolutionary sense, porcine BNP is more likely to be related to the corresponding human protein, than is a corresponding canine protein. It was thus unexpected that porcine BNP was unable to identify human NRP, and that a canine gene was needed to serve as an intermediate.

The source of the desired genes can be either a genomic library appropriate to the vertebrate species or a cDNA library from cells synthesizing the peptide. As explained below, although these peptides are synthesized in brain, they are also known to occur in atrial tissue at a lower level than the normally produced ANP. Therefore, the more readily accessible atrial tissue can also be used to prepare the cDNA library to be probed in preference to brain tissue. In this instance, high stringency and +/− hybridization can be used to distinguish the more predominant ANP-encoding DNA. Preparation of both genomic and cDNA libraries is well known in art; indeed, some genomic libraries are commercially available. Preferred techniques for preparing cDNA libraries are disclosed by Hyunh, V.T., et al., *DNA Cloning Techniques—A Practical Approach* (IRL Press, Oxford, 1984), and by Okayama and Berg, *Mol Cell Biol* (1983) 3:280-289. Preferably, the procedure exemplified below can, for example, be followed.

The genomic or cDNA library is then probed under nonstringent conditions (e.g., 20% formamide, 6×SSC at 37° C.) to obtain hybridizing sequences. The retrieved sequences can then be analyzed and sequenced according to standard procedures.

The entire pBNP-encoding DNA of FIG. 1 can be used as a probe, or an effective portion can be used. What constitutes an effective portion depends on the nature of the library being probed and can be determined experimentally. In general, if a genomic library is the source for retrieval of the desired gene, a segment of the pBNP-encoding cDNA extending from about residue 601-1300 is convenient. This segment bridges the intron which interrupts the coding sequence for the pBNP protein. Upstream portions of the sequence could also be used. Of course, there is no particular disadvantage in using the entire clone. On the other hand, if cDNA libraries are being investigated, it may be desirable to use only a portion of the cDNA which represents the ordinarily spliced coding regions. Thus, for example, a convenient probe might be a contiguous DNA sequence representing the pBNP codons (positions 660-723 and 1276-1289) or a somewhat smaller segment thereof.

It is understood, of course, that the actual probes may be sequences shown, or preferably their complements.

In practice, the porcine DNA of FIG. 1 was able to retrieve genes encoding related proteins in genomic libraries from other species, but was unable to retrieve human NRP directly. Genomic libraries from pig, rat, dog, cat and rabbit showed the ability to hybridize to the probe of FIG. 1 under at least one of the conditions:

(1) 50% formamide, 6×SSC, 5×Denhardt's, 10 mM sodium phosphate, 10 ug/ml sheared DNA at 42° C.; and (2) 20% formamide, 6 x SSC, 5×Denhardt's, 10 mM sodium phosphate, 10 ug/ml sheared DNA at 37° C.

Under both hybridization conditions, washing was at 1×SSC, 0.1% SDS at 50°-60° C. for 1 hour.

Human genomic DNA did not hybridize to the DNA sequence of FIG. 1 under these conditions, however it was possible to use canine NRP to obtain human NRP. The necessity to use the canine NRP sequence to obtain human NRP gene sequences could not, of course, be predicted.

By obtaining the canine DNA through use of the porcine probe, an insert having the sequence shown in FIG. 3 was obtained, was designated pdBNP-1, and was deposited at the American Type Culture Collection on 14 Dec. 1988 under Accession No. ATCC-67862. Using this sequence as a probe, a clone obtained from EcoRI-digested human genomic DNA was found which encodes a similar protein having natriuretic activity. This human DNA. has the sequence shown in FIG. 5, was designated phBNP-1, and was deposited at the American Type Culture Collection on 14 Dec. 1988 under Accession No. ATCC-67863.

The amino acid sequence encoding the putative prepro forms of peptides with natriuretic activity from porcine, canine, and human species are shown in FIG. 6. It is apparent that the porcine and canine species are more homologous in the region putatively responsible for natriuretic activity than the human sequence. Using the information in FIG. 6, a class of peptides having natriuretic activity can be defined. This class is of the formula:

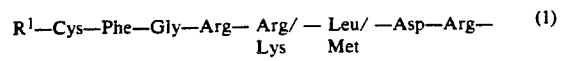

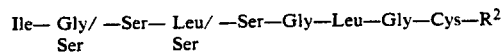

wherein R¹ is selected from the group consisting of:

(H);

Gly—;

Ser—Gly—;

Asp
Lys/ —Ser—Gly—;
Gly

Arg/ Asp/
His/ — Lys/ —Ser—Gly—;
Gln Gly

Arg/ Asp/
Met/ — His/ — Lys/ —Ser—Gly—;
Val Gln Gly

Arg/ Asp/
Thr/ — Met/ — His/ — Lys/ —Ser—Gly—;
Met Val Gln Gly

Arg/ Asp/
Lys— Thr/ — Met/ — His/ — Lys/ —Ser—Gly—;
Met Val Gln Gly

Arg/ Asp/
Pro—Lys— Thr/ — Met/ — His/ — Lys/ —Ser—Gly—;
Met Val Gln Gly

Arg/ Asp/
Ser—Pro—Lys— Thr/ — Met/ — His/ — Lys/ —Ser—Gly—;
Met Val Gln Gly or a 10- to 109-amino acid sequence shown as the native upstream sequence for porcine, canine or human BNP in FIG. 6, or a composite thereof;

R² is (OH), NH₂, or NR'R" wherein R' and R" are independently lower alkyl (1-4C) or is Asn/
Lys Asn/ —Val
Lys Asn/ —Val—Leu
Lys Asn/ —Val—Leu—Arg
Lys Asn/ —Val—Leu—Arg— Arg/
Lys             Lys Asn/ —Val—Leu—Arg— Arg/ — Tyr/
Lys             Lys      His or the amides (NH₂ or NR'R") thereof, with the proviso that if formula (1) is

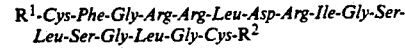

and R¹ is Asp-Ser-Gly-, R² cannot be Asn-Val-Leu-Arg-Arg-Tyr.

As used above, "composite" of the sequences shown as native upstream sequences for porcine, canine or human BNP or NRP in FIG. 6 refers to upstream sequences as there shown, where each position contains the alternative amino acids shown for all three species interchangeably. The composites of these sequences are constructed as were the composites for the specifically designated sequences in formula (1) and definitions of R¹ and R² above.

In addition, these peptide sequences can be modified by substituting one or two conservative amino acid substitutions for the positions specified, including substitutions which utilize the D rather than L form. As these peptides can be synthesized using standard solid-phase techniques, for example, it is not necessary to confine the conservative substitutions to amino acids encoded by genes.

Upon retrieval of the precursor gene encoding the BNP family for a particular vertebrate species, deduction of the BNP peptides associated with that species is a matter of translation of the determined sequence and identification of the processing site. Guidance is given by virtue of the pattern with respect to the atrial natriuretic peptide counterparts. It is believed that in analogy to the atrial peptides, the BNP protein are cyclic disulfides formed by oxidation of the cysteine residues at positions 4 and 20 of the sequence shown above for pBNP. The class of BNP peptides encoded for a particular species is believed to include truncated forms exocyclic to this disulfide bonded ring as well as extended forms of the pBNP shown, including peptides with one or two conservative amino acids substitutions in the sequence.

A deduced (or otherwise generated) peptide sequence falls within the scope of certain natriuretic proteins of the invention, provided that the DNA encoding it directly or indirectly hybridizes to the pBNP-encoding cDNA of FIG. 1 under conditions corresponding to the stringency represented by hybridization in buffer containing 20% formamide, 5×Denhardt's, 6×SSC, 100 mg/ml RNA, and 0.05% sodium pyrophosphate at 42° C., followed by washing at 60° C. at 1×SSC, 0.1% SDS, or under conditions (1) or (2) described above. In addition, the peptide encoded by this DNA must exhibit natriuretic activity assayed as described below.

By "direct hybridization" is meant that the DNA encoding the natriuretic peptide hybridizes to the DNA shown in FIG. 1 or an effective portion thereof per se. By "indirect hybridization" is meant that the DNA hybridizes to an DNA which is capable itself of hybridizing to the porcine BNP of FIG. 1. Thus, the human sequence shown in FIG. 5 indirectly hybridizes to the porcine BNP through the canine sequence of FIG. 3. However, porcine BNP did not hybridize directly to human NRP.

The invention is also directed to modified forms of the BNP proteins encoded by the cDNA of FIG. 1. One or two of the positions of these BNPs can be altered, so long as activity is retained. Conservative amino acid substitutions are preferred—that is, for example, aspartic/glutamic as acidic amino acids; lysine/arginine/histidine as basic amino acids; leucine/isoleucine, methionine/valine as hydrophobic amino acids; serine/glycine/alanine/threonine as hydrophilic amino acids. However, as the peptides need not be prepared by recombinant methods or from the gene, the substitutions may include nonencoded amino acids such as the D- or beta-amino forms.

B. Production of BNP and NRP

The BNP and NRP of the invention can be produced in a variety of ways, including using recombinant methods.

The retrieved genes encoding BNP and NRP peptides can then be manipulated and expressed using a variety of recombinant systems. Peptides having the sequence encoded by any subsegment of the retrieved gene can be obtained in host systems which do not process the translated protein by proper design of the expression system. For example, the expression system is constructed by placing an ATG start codon immediately preceding the desired N-terminus and a termination codon after the desired C-terminus, with appropriate modification of any adjacent sequences. The desired coding sequence is then ligated in operable linkage to a control system functional in procaryotic or eucaryotic hosts, as desired. A large number of control systems are now known in the art.

As the natriuretic peptide precursors are evidently processed in certain eucaryotic systems, attention should be paid to the choice of the recombinant host, or it is possible to prevent processing by modification of the gene sequence so as to encode substitute amino acids in positions believed to be susceptible to cleavage by proteolytic enzymes. For example, the arginine immediately upstream from the aspartic acid residue at position one of pBNP could be replaced by a threonine residue, thus rendering the resulting peptide non-susceptible to trypsin cleavage at that site. In the alternative, expression can be effected in hosts which are deficient in enzymes capable of processing these peptides.

As the genes encoding the families of natriuretic-related peptides for various vertebrate species are made accessible by the availability of the probes constructed from pBNP-encoding DNA, these genes can be manipulated by replacing the codons for one or more amino acids by site directed mutagenesis, to obtain sequences encoding analogs of these peptides which retain natriuretic activity.

Construction of expression vectors and recombinant production from the appropriate DNA sequences are performed by methods known in the art per se.

Expression can be in procaryotic or eucaryotic systems. Procaryotes most frequently are represented by various strains of *E. coli*. However, other microbial strains may also be used, such as bacilli, for example *Bacillus subtilis*, various species of *Pseudomonas*, or other bacterial strains. In such procaryotic systems, plasmid vectors which contain replication sites and control sequences derived from a species compatible with the host are used. For example, *E. coli* is typically transformed using derivatives of pBR322, a plasmid derived from an *E. coli* species by Bolivar et al., *Gene* (1977) 2:95. Commonly used procaryotic control sequences, which are defined herein to include promoters for transcription initiation, optionally with an operator, along with ribosome binding site sequences, including such commonly used promoters as the beta-lactamase (penicillinase) and lactose (lac) promoter systems (Chang et al., *Nature* (1977) 198:1056) and the tryptophan (trp) promoter system (Goeddel et al., *Nucleic Acids Res* (1980) 8:4057) and the lambda-derived $P_L$ promoter and N-gene ribosome binding site (Shimatake et al., *Nature* (1981) 292:128). Any available promoter system compatible with procaryotes can be used.

The expression systems useful in the eucaryotic hosts comprise promoters derived from appropriate eucaryotic genes. A class of promoters useful in yeast, for example, include promoters for synthesis of glycolytic enzymes, including those for 3-phosphoglycerate kinase (Hitzeman et al., *J Biol Chem* (1980) 255:2073). Other promoters include those from the enolase gene (Holland, M.J., et al. *J Biol Chem* (1981) 256:1385) or the Leu2 gene . obtained from YEp13 (Broach, J., et al., *Gene* (1978) 8:121).

Suitable mammalian promoters include metallothionein, the early and late promoters from SV40 (Fiers et al., *Nature* (1978) 273:113) or other viral promoters such as those derived from polyoma, adenovirus II, bovine papilloma virus or avian sarcoma viruses. Suitable viral and mammalian enhancers are cited above. In the event plant cells are used as an expression system, the nopaline synthesis promoter is appropriate (Depicker, A., et al., *J Mol Appl Gen* (1982) 1:561).

The expression system is constructed from the foregoing control elements operably linked to the BNP sequences using standard methods, employing standard ligation and restriction techniques which are well understood in the art. Isolated plasmids, DNA sequences, or synthesized oligonucleotides are cleaved, tailored, and religated in the form desired.

Site specific DNA cleavage is performed by treating with the suitable restriction enzyme (or enzymes) under conditions which are generally understood in the art, and the particulars of which are specified by the manufacturer or these commercially available restriction enzymes. See, e.g., New England Biolabs, Product Catalog. In general, about 1 ug of plasmid or DNA sequence is cleaved by one unit of enzyme in about 20 ul of buffer solution; in the examples herein, typically, an excess of restriction enzyme is used to insure complete digestion of the DNA substrate. Incubation times of about 1 hr to 2 hr at about 37° C. are workable, although variations can be tolerated. After each incubation, protein is removed by extraction with phenol/chloroform, and may be followed by ether extraction, and the nucleic acid recovered from aqueous fractions by precipitation with ethanol followed by running over a Sephadex G-50 spin column. If desired, size separation of the cleaved fragments may be performed by polyacrylamide gel or agarose gel electrophoresis using standard techniques. A general description of size separation is found in *Methods in Enzymology* (1980) 65:499-560.

Restriction cleaved fragments may be blunt ended by treating with the large fragment of *E. coli* DNA polymerase I (Klenow) in the presence of the four deoxynucleotide triphosphates (dNTPs) using incubation times of about 15 to 25 min at 20° to 25° C. in 50 mM Tris pH 7.6, 50 mM NaCl, 6 mM $MgCl_2$, 6 mM DTT and 5-10 uM dNTPs. The Klenow fragment fills in at 5' sticky ends but chews back protruding 3' single strands, even though the four dNTPs, are present. If desired, selective repair can be performed by supplying only one of the, or selected, dNTPs within the limitations dictated by the nature of the sticky ends. After treatment with Klenow, the mixture is extracted with phenol/chloroform and ethanol precipitated followed by running over a Sephadex G-50 spin column. Treatment under appropriate conditions with S1 nuclease results in hydrolysis of any single-stranded portion.

Synthetic oligonucleotides are prepared using commercially available automated oligonucleotide synthesizers. Kinasing of single strands prior to annealing or for labeling is achieved using an excess, e.g., approximately 10 units of polynucleotide kinase to 0.1 nmole substrate in the presence of 50 mM Tris, pH 7.6, 10 mM $MgCl_2$, 5 mM dithiothreitol, 1-2 mM ATP, 1.7 pmoles $^{32}P$-ATP (2.9 mCi/mmole), 0.1 mM spermidine, 0.1 mM EDTA.

Ligations are performed in 15-30 ul volumes under the following standard conditions and temperatures: 20 mM Tris-HCl pH 7.5, 10 mM $MgCl_2$, 10 mM DTT, 33 ug/ml BSA, 10 mM-50 mM NaCl, and either 40 uM ATP, 0.01-0.02 (Weiss) units T4 DNA ligase at 0° C. (for "sticky end" ligation) or 1 mM ATP, 0.3-0.6 (Weiss) units T4 DNA ligase at 14° C. (for "blunt end" ligation). Intermolecular "sticky end" ligations are usually performed at 33-100 ug/ml total DNA concentrations (5-100 nM total end concentration). Intermolecular blunt end ligations (usually employing a 10- to 30-fold molar excess of linkers) are performed at 1 uM total ends concentration.

In vector construction employing "vector fragments," the vector fragment is commonly treated with bacterial alkaline phosphatase (BAP) in order to remove the 5' phosphate and prevent religation of the vector. BAP digestions are conducted at pH 8 in approximately 150 mM Tris, in the presence of $Na^+$ and $Mg^{+2}$ using about 1 unit of BAP per ug of vector at 60° C. for about 1 hr. In order to recover the nucleic acid fragments, the preparation is extracted with phenol/chloroform and ethanol precipitated and desalted by application to a Sephadex G-50 spin column. Alternatively, religation can be prevented in vectors which have been double digested by additional restriction enzyme digestion of the unwanted fragments.

For portions of vectors derived from cDNA or genomic DNA which require sequence modifications, site specific primer directed mutagenesis is used. This is conducted using a primer synthetic oligonucleotide complementary to a single stranded phage DNA to be mutagenized except for limited mismatching, representing the desired mutation. Briefly, the synthetic oligonucleotide is used as a primer to direct synthesis of a stand complementary to the phage, an the resulting double-stranded DNA is transformed into a phage-supporting host bacterium. Cultures of the transformed bacteria are plated in top agar, permitting plaque formation from single cells which harbor the phage.

Theoretically, 50% of the new plaques will contain the phage having, as a single strand, the mutated form; 50% will have the original sequence. The resulting plaques are hybridized with kinased synthetic primer at a temperature which permits hybridization of an exact match, but at which the mismatches with the original strand are sufficient to prevent hybridization. Plaques which hybridize with the probe are then picked, cultured, and the DNA recovered. Details of site specific mutation procedures are described below in specific examples.

Correct ligations for plasmid construction can be confirmed by first transforming *E. coli* strain MM294 obtained from *E. coli* Genetic Stock Center, CGSC #6135, or other suitable host with the ligation mixture. Successful transformants are selected by ampicillin, tetracycline or other antibiotic resistance or using other markers depending on the mode of plasmid construction, as is understood in the art. Plasmid from the transformants are then prepared according to the method of Clewell, D.B., et al., *Proc Natl Acad Sci USA* (1969) 62:1159, optionally following chloramphenicol amplification (Clewell, D.B., *J Bacteriol* (1972) 110:667). The isolated DNA is analyzed by restriction and/or sequenced by the dideoxy method of Sanger, F., et al., *Proc Natl Acad Sci USA* (1977) 74:5463 as further described by Messing et al., *Nucleic Acids Res* (1981) 9:309, or by the method of Maxam et al., *Methods in Enzymology* (1980) 65:499.

The constructed vector is then transformed into a suitable host.

Depending on the host cell used, transformation is done using standard techniques appropriate to such cells. The calcium treatment employing calcium chloride, as described by Cohen, S.N., *Proc Natl Acad Sci USA* (1972) 69:2110, or the RbCl method described in Maniatis et al., *Molecular Cloning: A Laboratory Manual* (1982), Cold Spring Harbor Press, p. 254, is used for procaryotes or other cells which contain substantial cell wall barriers. Infection with *Agrobacterium tumefaciens* (Shaw, C.H., et al., *Gene* (1983) 23:315) is used for certain plant cells. For mammalian cells without such cell walls, the calcium phosphate precipitation method of Graham and van der Eb, *Virology* (1978) 52:546, is preferred. Transformations into yeast are carried out according to the method of Van Solingen, P., et al., *J Bacter* (1977) 130:946, and Hsiao, C.L., et al., *Proc Natl Acad Sci USA* (1979) 76:3829.

The transformed cells are then cultured under conditions favoring expression of the BNP sequence and the recombinantly produced protein recovered from the culture.

In addition to recombinant production, peptides whose deduced sequences are sufficiently short to make direct peptide synthesis practical can be prepared using standard solid-phase techniques.

Thus, compounds within the scope of the present invention can be synthesized chemically by means well known in the art such as, e.g., solid-phase peptide synthesis. The synthesis is commenced from the carboxy-terminal end of the peptide using an alpha-amino protected amino acid. t-Butyloxycarbonyl (Boc) protective groups can be used for all amino groups even though other protective groups are suitable. For example, Boc-Val-OH, Boc-Leu-OH, Boc-Arg-OH or Boc-Tyr-OH (i.e., selected BNP analog carboxy-terminal amino acids) can be esterified to chloromethylated polystyrene resin supports. The polystyrene resin support is preferably a copolymer of styrene with about 0.5 to 2% divinyl benzene as a cross-linking agent which causes the polystyrene polymer to be completely insoluble in certain organic solvents. See Stewart, et al., *Solid-Phase Peptide Synthesis* (1969), W.H. Freeman Co., San Francisco, and Merrifield, *J Am Chem Soc* (1963) 85:2149–2154. These and other methods of peptide synthesis are also exemplified by U.S. Pat. Nos. 3,862,925; 3,842,067; 3,972,859; and 4,105,602.

The synthesis may use manual techniques or automatically employing, for example, an Applied Biosystems 430A Peptide Synthesizer (Foster City, Calif.) or a Biosearch SAM II automatic peptide synthesizer (Biosearch, Inc., San Rafael, Calif.), following the instructions provided in the instruction manual supplied by the manufacturer.

Of course, since automated synthesis also permits control of the sequence, the above-mentioned modifications to the amino acid sequence obtained by modifying the gene as described above are available using this method of synthesis. In addition, it is not necessary that the substituted amino acid be encoded by a gene. Therefore, the D-forms or beta-amino acids can be substituted for those natively present.

The foregoing methods to synthesize the BNP of the invention are not intended to be limiting, and the BNP of the invention may be prepared in any convenient manner. The BNP is required only to be encoded by a gene which hybridizes under the above-specified stringent conditions to the cDNA of FIG. 1, and to show natriuretic activity in the receptor assay described below.

C. Assay Systems

The members of the natriuretic peptides (NPs) of the invention from the various vertebrate species and the modifications thereof can be verified to have the required natriuretic activity using standard methods to assay such activity. A number of systems both in vitro and in vivo are available. The simplest form of in vitro test is a binding assay testing the affinity of the peptides for receptors in the kidney and other sites responsible for influencing the clearance of the endogenous natriuretic compounds. Accordingly, in a manner analogous to the assay procedure for the atrial derived natriuretic peptides, natriuretic activity in general can be assayed by the ability of the candidate peptide to compete with pBNP which has been labeled, for example, by iodination for binding to receptors from cultured bovine aortic smooth muscle (BASM) cells and bovine aortic endothelial (BAE) cells. The competition is diagnostic for the binding to the relevant clearance receptors. In addition, levels of cyclic GMP can be measured in these same cells and are diagnostic for binding of the peptide to relevant biological receptors responsible for the observed in vivo bioactivity.

To fall within the scope of the compositions claimed herein, the candidate peptide must be encoded by a gene sequence capable of hybridizing directly or indirectly to pBNP-encoding DNA under the stringency conditions set forth herein, or be defined by formula (1) or its modified forms as set forth above, and must show activity in an in vitro receptor binding assay; either binding to the clearance receptors as shown by the competition assay, or to the effector receptors as shown by the alteration of cyclic GMP levels, or both. The peptide may or may not have direct biological activities associated with pBNP, such as cyclic GMP activity, if it inhibits clearance receptor binding in a manner that correlates with an in vivo test for natriuretic and diuretic activities. The peptides may also be vasodilators.

Receptor Binding Assays

Specific ANP receptor sites have been identified on target tissues, such as kidney, adrenal, blood vessels, and cultured cells. Napier, M.A., et al., *Proc Nat Acad Sci USA* (1984) 81:5946–5940; DeLean, A., et al., *Endocrinology* (1984) 115:1636–1638; Schenk, D.B., et al., *Biochem Biophys Res Comm* (1985) 127:433–442. Such tissues will have receptors for BNP binding which may or may not be identical to those for ANP. Since the binding of ANP or ANP analogs to these specific receptor sites is presumptively a prerequisite of biological activity, binding of BNP-associated peptides, or their modified forms to these receptors is considered predictive of biological activity.

An assay has been developed, generally in accordance with the disclosure of Schenk, supra, and Scarborough, R.M., et al., *J Biol Chem* (1986) 261:12960–12964, which evaluates the ability of ANP analogs to compete with a labeled native ANP for binding to cultured BASM and BAE cells. A similar assay, utilizing labeled pBNP can be used to evaluate candidate BNP family peptides. The pBNP (shown above) was iodinated on the carboxy-terminal Y residue and is identified as ($^{125}$I)-pBNP. Analogous "competitive displacement" receptor binding assays are considered commonplace in the art for examining specific ligand-receptor interactions.

In this assay, 0.5 nM ($^{125}$I)-pBNP or ($^{125}$I)-human NRP is incubated in each individual sample of BASM cells in the presence of varying amounts of unlabeled pBNP, hNRP, dNRP or a candidate peptide encoded by a gene hybridizing to pBNP-encoding cDNA.

Increasing concentrations of pBNP, or successful candidate peptide effectively prevent ($^{125}$I)-pBNP binding to BASM cell-associated receptors. The concentration of unlabeled peptide at which 50% of maximal ($^{125}$I)-pBNP binding is displaced is called Ki(app) and reflects receptor-binding affinity. Therefore, a peptide with a Ki(app)=100nM displays substantially weaker interaction with a receptor than peptide with a Ki(app)=10nM. Assuming these BNP analogs act at one or more BNP receptor sites, then increased receptor affinity should reflect increased biological potency.

The choice of the proper natriuretic peptide for the competition assay above should be made with regard to the peptide of the invention being tested. The receptors utilized by, for example, ANP and BNP may be the same or different. Alternate species forms of either may be used as competitors in suitable assay reactions for candidate peptides of formula (1).

Whole Mammal Bioassays

The biological activity of NP sequences of the present invention (which show activity in the receptor assay above), can be confirmed in anesthetized rats and dogs. The correlation of receptor binding affinity and in vivo effects demonstrates the predictive value of the receptor assays for biological activity.

1. Diuresis and Natriuresis in Anesthetized Rats

In one method, cannulae are placed in the left and right ureters and femoral vein of anesthetized rats and urine is collected from the ureters. NP compositions are administered via the femoral vein. Prior to infusing the NP, saline is infused for 30 minutes, urine is collected for 6 five-minute baseline periods and urine volume is determined gravimetrically.

Following these baseline collection periods, various NPs are infused for 30 or 60 minutes and urine volume is measured in five-minute periods during infusion and for 60 minutes following infusion (at which time rats are returned to saline). Data are examined by averaging urine flow rates for six five-minute baseline control periods immediately preceding infusion, and comparing values during and after administration of NP with the "baseline" control values. Responses to NP are thus evaluated and plotted as the percent of baseline control responses. Responses to peptides that are substantially above baseline ± SD can thus be interpreted as being statistically significant increases.

2. Diuresis and Natriuresis in Anesthetized Dogs

The biological activity of NP of the present invention can also be confirmed in pentobarbital-anesthetized dogs. In these examples, cannulae are placed in the left and right ureters or urinary bladder and femoral vein of anesthetized dogs and urine is collected. NP is administered via the femoral vein. Prior to infusing NP, saline is infused for 30 minutes and urine is then collected for three ten-minute collection periods. Urine volume is determined gravimetrically and urine sodium is determined photometrically.

Following these three baseline collection periods, the selected NP is infused for 60 minutes and urinary flow and urinary sodium excretion measured for an additional 60 minutes following infusion. During infusion (60 minutes) and recovery (60 minutes), ten-minute collection periods are obtained. Control animals which received only saline are studied in parallel.

Data are examined by comparing urine flow rates and sodium excretion rates for dogs infused with various NP portions against control animals infused with saline.

Isolated Tissue Bioassays

The effect of NP in vivo may be achieved solely by the ability to potentiate the effect of endogenous NP, through blockage of the receptors involved in binding and clearing endogenous NPs. To the extent that this is the case for a particular NP, it could be expected that the diuretic and natriuretic effects of the NP would be diminished or eliminated in isolated tissue where NPs are not present unless specifically supplied.

Thus, NP compositions fall within the scope of the invention even if their activity in isolated tissue bioassays is low; however, activity in these assays may also be present.

D. Utility and Administration

Briefly, the natriuretic peptides of the invention are useful in treatment of disorders associated with high levels of extracellular fluids such as hypertension. The compounds are administered in conventional formulations for peptides such as those described in *Remington's Pharmaceutical Sciences*, Mack Publishing Company, Easton, Pa. (latest edition). Preferably, the peptides are administered by injection, preferably intravenously, using appropriate formulations for this route of administration. Dosage levels are on the order of 0.01-100 ug/kg of subject.

These compounds, and compositions containing them, can find use as therapeutic agents in the treatment of various edematous states such as, for example, congestive heart failure, nephrotic syndrome and hepatic cirrhosis, in addition to hypertension and renal failure due to ineffective renal perfusion or reduced glomerular filtration rate. The natriuretic peptides of the invention are particularly effective in the treatment of congestive heart failure.

Thus the present invention also provides compositions containing an effective amount of compounds of the present invention, including the nontoxic addition salts, amides and esters thereof, which may, alone, serve to provide the above-recited therapeutic benefits Such compositions can also be provided together with physiologically tolerable liquid, gel or solid diluents, adjuvants and excipients.

These compounds and compositions can be administered to mammals for veterinary use, such as with domestic animals, and clinical use in humans in a manner similar to other therapeutic agents In general, the dosage required for therapeutic efficacy will range from about 0.001 to 100 ug/kg, more usually 0.01 to 100 ug/kg of the host body weight. Alternatively, dosages within these ranges can be administered by constant infusion over an extended period of time, usually exceeding 24 hours, until the desired therapeutic benefits have been obtained Typically, such compositions are prepared as injectables, either as liquid solutions or suspensions; solid forms suitable for solution in, or suspension in, liquid prior to injection may also be prepared. The preparation may also be emulsified. The active ingredient is often mixed with diluents or excipients which are physiologically tolerable and compatible with the active ingredient. Suitable diluents and excipients are, for example, water, saline, dextrose, glycerol, or the like, and combinations thereof. In addition, if desired the compositions may contain minor amounts of auxiliary substances such as wetting or emulsifying agents, stabilizing or pH-buffering agents, and the like.

The compositions are conventionally administered parenterally, by injection, for example, either subcutaneously or intravenously. Additional formulations which are suitable for other modes of administration include suppositories, intranasal aerosols, and, in some cases, oral formulations. For suppositories, traditional binders and excipients may include, for example, polyalkylene glycols or triglycerides; such suppositories may be formed from mixtures containing the active ingredient in the range of 0.5% to 10% preferably 1%-2%. Oral formulations include such normally employed excipients as, for example, pharmaceutical grades of mannitol, lactose, starch, magnesium stearate, sodium saccharin, cellulose, magnesium carbonate, and the like. These compositions take the form of solutions, suspensions, tablets, pills, capsules, sustained-release formulations, or powders, and contain 10%-95% of active ingredient, preferably 25%-70%.

The peptide compounds may be formulated into the compositions as neutral or salt forms. Pharmaceutically acceptable nontoxic salts include the acid addition salts (formed with the free amino groups) and which are formed with inorganic acids such as, for example, hydrochloric or phosphoric acids, or organic acids such as, for example, hydrochloric or phosphoric acids, or such organic acids as acetic, oxalic, tartaric, mandelic, and the like. Salts formed with the free carboxyl groups may be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

In addition to the compounds of the present invention which display natriuretic, diuretic or vasorelaxant activity, compounds of the present invention can also be employed as intermediates in the synthesis of such useful compounds. Alternatively, by appropriate selection, compounds of the present invention whose activity levels are reduced or eliminated entirely can serve to modulate the activity of other diuretic, natriuretic or vasorelaxant compounds, including compounds outside the scope of the present invention, by, for example, binding to clearance receptors, stimulating receptor turnover, or providing alternate substrates for degradative enzyme or receptor activity and thus inhibiting these enzymes or receptors. When employed in this manner, such compounds can be delivered as admixtures with other active compounds or can be delivered separately, for example, in their own carriers.

Compounds of the present invention can also be used for preparing antisera for use in immunoassays employing labeled reagents, usually antibodies. Conveniently, the polypeptides can be conjugated to an antigenicity-conferring carrier, if necessary, by means of dialdehydes, carbodiimide or using commercially available linkers. These compounds and immunologic reagents may be labeled with a variety of labels such as chromophores, fluorophores such as, e.g., fluorescein or rhodamine, radioisotopes such as $^{125}I$, $^{35}S$, $^{14}C$, or $^{3}H$, or magnetized particles, by means well known in the art.

These labeled compounds and reagents, or labeled reagents capable of recognizing and specifically binding to them, can find use as, e.g., diagnostic reagents. Samples derived from biological specimens can be assayed for the presence or amount of substances having a common antigenic determinant with compounds of the present invention. In addition, monoclonal antibodies can be prepared by methods known in the art, which antibodies can find therapeutic use, e.g., to neutralize overproduction of immunologically related compounds in vivo.

Suitable subjects include those animals having conditions of high water or sodium ion accumulation. Both veterinary and therapeutic uses in humans are appropriate.

The following examples are intended to illustrate but not to limit the invention.

Example 1

Retrieval of Porcine BNP-Encoding DNA

Porcine heart tissue frozen in liquid nitrogen was obtained and separated roughly into atrial and ventricular portions. Frozen atrial tissue (5 g) was first pulverized in a mortar and pestle, then ground to a powder in a tissuemizer and liquefied in a large volume (25 ml) of 5 M guanidinium thiocyanate containing 50 mM Tris (pH 7.5), 5 mM EDTA, and 5% beta-mercaptoethanol. Sarcosyl was then added to 2% and the sample was incubated at 65° C. for 2 min whereupon insoluble material was removed by centrifugation at 7000×g for 10 min. Total RNA was isolated from this supernatant by adding 2.5 g of CsCl, layering over a 10 ml cushion of 5.8 M CsCl and centrifuging again at 25,000 rpm for 12 hr. The supernatant was subsequently aspirated and the pellet dissolved in buffer containing Tris (50 mM), EDTA (5 mM), and beta-mercaptoethanol (2%). The RNA solution was then phenol extracted once and precipitated with ethanol. Poly A+ RNA was isolated by oligo dT cellulose chromatography.

Double-stranded DNA complementary to the porcine atrial mRNA (5 ug) was synthesized by the RN.Ase H method. The cDNA was then methylated by standard methods and EcoRI linkers ligated and digested. The entire cDNA was then ligated into previously prepared lambda phage arms and packaged according to standard methods. Plating of this packaging reaction gave a library with ~1.75×10⁵ randomly isolated phage from this library showed that almost all (>95%) had inserts in the 1-5 kb range.

Probes were designed to detect the pBNP cDNA. As shown in FIG. 2, conservation with respect to human ANP cDNA was assumed in constructing oligo 3351. Thus, the human ANP-encoding sequence shown in the figure was modified only to the extent required to obtain a sequence encoding pBNP. The second oligo, 3352, was another 60-mer designed according to mammalian codon preference and preferring G and T over A and C. The additional 60-mer 3376 was synthesized to match the human ANP sequence so as to eliminate false positives.

Approximately 300,000 phage from the above library were plated and lifted with nitrocellulose filters in duplicate. Series A (15 nitrocellulose filters) were denatured, neutralized, baked for 2 hr and prehybrodized for 2 hr in hybridization buffer (20% formamide, 5×Denhardt's solution, 6×SSC, 0.05% pyrophosphate, 100 ug/ml salmon sperm DNA). Labeled oligonucleotide probe (3351, $1.5 \times 10^7$ cpm) was then added and the filters incubated overnight at 42° C. Filters were subsequently washed in 6× SSC, 0.1% SDS at 20° C. for 40 min., and then twice in 1× SSC at 65° C. for 10 min. Series B was treated in the same manner except oligo 3352 was used. Final washing was at 60° C. in this case. In both cases filters were dried and subjected to autoradiography. Approximately 450 positives (0.2% of total clones plated) were obtained when probing with oligo 3351 and most of these are believed to be porcine ANP based on previous screening with this oligo. Four clones in series B hybridized to oligo 3352. These hybrids were stable at 60° C. but not at 65° C. Of these four, only clone 14 hybridized with oligo 3351 also, and this was picked and subjected to another round of purification. The purified phage was then grown, and the DNA was isolated by centrifugation at 36,000 rpm over a CsCl step gradient, phenol extracted, dialyzed, and ethanol precipitated. The phage DNA contained a 1.5 kb DNA insert when subjected to restriction analysis with EcoRI. This insert was then subcloned into an M13 sequencing vector and the sequence determined. The abundance of this BNP mRNA appeared about 400-fold lower than ANP in this library, or 0.0005%.

The DNA sequence of the insert from clone 14 is shown in FIG. 1. The coding region for BNP is present within the clone; however, it is interrupted by what appears to be an intron at residue $Val_{22}$ of the 26-amino acid BNP. Therefore, it appears that this clone contains an unprocessed mRNA with one or more introns present.

EXAMPLE 2

Identification of the Upstream Intron

As set forth above, the DNA sequence of FIG. 1 shows a change in reading frame and, furthermore, by analogy to the ANP-encoding gene as described by Greenberg et al. (supra), may contain an upstream intron. In order to locate the position of this intron, the sequences surrounding its putative location were used as primers in an amplification procedure to obtain spliced DNA lacking the intron.

Poly A+ RNAs were isolated from porcine atrial tissue using the guanidinium isothiocyanate method of Chirgwin, J.M., *Biochemistry* (1979) 18:5294–5299, followed by oligo-dT cellulose chromatography. Approximately 2 ug of the porcine atrial mRNA was incubated with 400 ng of oligonucleotide 3895 (supra) as primer in a 20 ul reaction containing 0.5 mM dNTPs, 50 mM Tris-HCl, pH 8.3, 10 mM magnesium chloride, 10 units of RNasin, and 50 units of reverse transcriptase. Subsequent amplification of the resulting DNA was performed as described by Saiki, R.K., *Science* (1988) 239:487–491. After incubation for 1 hr at 37° C., half of the reaction was diluted to 100 ul in 67 mM Tris-HCl, pH 8.8, 6.7 mM magnesium chloride, 16.6 mM ammonium sulfate, 10 mM mercaptoethanol, 6.7 uM EDTA, 1 mM dNTPs, 10% DMSO, and 400 ng of each primer oligonucleotide. The oligonucleotide primers were those corresponding to bases 100–123 (identity strand) and 652–685 (complementary strand) of the pBNP clone shown in FIG. 1.

The reaction mixture was denatured by boiling for 5 min followed by incubation at 42° C. to allow primer annealing. *Thermus aquaticus* polymerase (3 units) was added and the sample further incubated at 72° C. for 3 min. The cycle (98° C., 1 min; 43° C., 1 min; 72° C., 3 min) was repeated 30 times without addition of additional polymerase. The extended reaction was conducted under a 100 ul layer of mineral oil, and a 10 ul aliquot was removed and analyzed by standard agarose gel electrophoresis. The resulting DNA fragments were visualized after staining with ethidium bromide and purified by preparative agarose gel electrophoresis. The amplified DNA fragment was then kinased, ligated into M13, and sequenced.

Two DNA sequences resulted from this reaction: one of approximate 650 bp was in low relative amount and was presumably the unspliced version; the more abundant, approximately 350 bp, band was assumed to be the fully processed DNA and, indeed, showed the sequence set forth in FIG. 1 between the reverse arrows at positions 100–684.

EXAMPLE 3

Retrieval of NRP Encoding Genes

The entire 1504-base sequence in FIG. 1, or a shorter segment constituting bases 601–1300 is used as a probe to obtain the genes encoding analogous NRP peptides from other vertebrate species. (As discussed in Example 5 below, however, human NRP was not obtained by this direct procedure.) In this approach, blots of genomic DNA are used as substrate. Approximately 10 ug of genomic DNA from the liver of the appropriate species is digested with BamHI or PstI overnight, and the digested DNA precipitated with ethanol and electrophoresed on 0.8% agarose gels. The gels are blotted onto nitrocellulose filters overnight, and the filters then denatured, baked and prehybridized at 42° C. in prehybridization buffer (20% formamide, 5× Denhardt's 6× SSC, 100 mg/ml RNA, 0.05% sodium pyrophosphate)

The cDNA is labeled by nick-translation and hybridized to two panels from the same gel at 42° C. overnight in the prehybridization buffer. The filters are then washed in 1× SSC, 0.1% SDS at 60° C. and 65° C. and exposed to autoradiographic film.

The genes encoding the analogous NRPs in the particular species are then amplified and sequenced according to standard techniques. The deduced sequences can be manipulated to provide suitable restriction sites for insertion into expression systems and to provide desired stop and start codons by site-directed mutagenesis.

Genomic DNA from pig, rat, dog, cat, rabbit and human organisms were probed on Southern blots using the cDNA illustrated in FIG. 1 herein under two different hybridization conditions:

(1) 50% formamide, 6× SSC, 5× Denhardt's, 10 mM sodium phosphate, 10 ug/ml sheared DNA at 42° C.; and (2) 20% formamide, 6× SSC, 5× Denhardt's, 10 mM sodium phosphate, 10 ug/ml sheared DNA at 37° C.

Washing in both cases was in 1× SSC, 0.1% SDS at 50°–60° C. for 1 hr.

Hybridization did not occur between pBNP and human DNA.

EXAMPLE 4

Retrieval of Canine NRP

A dog genomic library obtained from Clontech Inc. yielded 2 clones under the condition (1) of Example 3 above and the DNA from these identified clones was digested with HaeIII or AluI and subcloned into M13. The resulting plaques were screened for hybridization to the porcine probe, and positive clones were sequenced. The identity of the clone was confirmed by detection of the BNP-encoding sequence of FIG. 1, and the 2.9 kb HindIII fragment containing the entire gene was then subcloned into pBR322, and designated pdBNP-1. The DNA sequence of the portion of this clone encoding the BNP gene is shown in FIG. 3, and the pdBNP-1 plasmid was deposited at the American Type Culture Collection on 14 Dec. 1988 and has Accession No. ATCC-67862.

EXAMPLE 5

Retrieval of Human NRP

A human genomic library failed to yield signals corresponding to hybridization with the probe using the porcine DNA of FIG. 1 as described in Example 3. Using pdBNP-1 as a probe under condition (1) of Example 3 above produced several distinct bands that could be visualized in blots of digested human genomic DNA, as shown in FIG. 4. A preparative agarose gel was utilized to isolate EcoRI-digested human genomic DNA in the 6–7 kb size range, which isolated DNA was then cloned into lambda-ZAP2 (Strategene Inc.), packaged, and the resulting mini-library was screened using the hybridization condition (1) of Example 3 above. Seven positive signals were purified and the insert subcloned into pBLUSCRIPT vector. The sequences of the M13 subclones of hybridization-positive HaeIII and AluI-digested plasmid DNA were determined. The sequence of the coding region of the plasmid, phBNP-1, is shown in FIG. 5 and the plasmid was deposited at the American Type Culture Collection on 14 Dec. 1988 with Accession No. ATCC-67863.

Using the intron splice junction consensus sequences described by Mount, S., *Nucleic Acids Res* (1982) 10:459–472, it appears that the first exon of the human cDNA sequence contains two extra amino acids in the BNP precursor region as compared to the porcine sequence. This can be verified by PCR amplification of human atrial RNA.

We claim:

1. A peptide having natriuretic activity of the formula $R^1$-Cys-Phe-Gly-Arg-Arg-Leu-Asp-Arg-Ile-Gly-Ser-Leu-Ser-Gly-Leu-Gly-Cys-$R^2$ wherein $R^1$ is selected from (H);

Gly—;

Ser—Gly—;

Gly—Ser—Gly—;

Gln—Gly—Ser—Gly—;

Val—Gln—Gly—Ser—Gly—;

Met—Val—Gln—Gly—Ser—Gly—;

Lys—Met—Val—Gln—Gly—Ser—Gly—;

Pro—Lys—Met—Val—Gln—Gly—Ser—Gly—,

Ser—Pro—Lys—Met—Val—Gln—Gly—Ser—Gly—; and $R^3$—Ser—Pro—Lys—Met—Val—Gln—Gly—Ser—Gly—;

wherein $R^3$ is the 102 amino acid sequence shown as positions 1–99 for the human protein in FIG. 6, or a C-terminal portion thereof, and $R^2$ is (OH), $NH_2$, NHR' or NR'R" wherein R' and R" are independently lower alkyl (1–4C) or $R^2$ is Lys;

Lys-Val;

Lys-Val-Leu;

Lys-Val-Leu-Arg;

Lys-Val-Leu-Arg-Arg;

Lys-Val-Leu-Arg-Arg-His;

or the amides ($NH_2$, NHR' or NR'R") thereof.

2. A pharmaceutical composition for inducing natriuresis, diuresis and/or vasodilation in a subject which composition comprises an effective amount of the peptide of claim 1 in admixture with a suitable pharmaceutical excipient.

3. A method to induce natriuresis, diuresis and/or vasodilation in a subject which method comprises administering to said subject in need of such treatment an effective amount of the peptide of claim 1 or a pharmaceutical composition thereof.

4. The peptide of claim 1 wherein $R^1$ is Ser-Pro-Lys-Met-Val-Gln-Gly-Ser-Gly- and $R^2$ is Lys-Val-Leu-Arg-Arg-His or the amide thereof.

* * * * *

UNITED STATES PATENT AND TRADEMARK OFFICE
CERTIFICATE OF CORRECTION

PATENT NO. : 5,114,923

DATED : 5/19/92

INVENTOR(S) : Jeffrey J. Seilhamer, John A. Lewicki, Robert M. Scarborough

It is certified that error appears in the above-identified patent and that said Letters Patent is hereby corrected as shown below:

In claim 1, column 24, lines 3-4, please delete the sequence and substitute therefor:

$R^1$-Cys-Phe-Gly-Arg-Lys-Met-Asp-Arg-Ile-Ser-Ser-Ser-Ser-Gly-Leu-Gly-Cys-$R^2$

On the title page, item [54] and in column 1, lines 2-5, please delete the title and substitute therefor:

PRODUCTION OF NOVEL NATRIURETIC AND VASODILATOR PEPTIDES

Signed and Sealed this

Fourteenth Day of July, 1992

Attest:

DOUGLAS B. COMER

Attesting Officer

Acting Commissioner of Patents and Trademarks